US012698325B2

(12) United States Patent

Klapproth et al.

(10) Patent No.: US 12,698,325 B2

(45) Date of Patent: Aug. 4, 2026

(54) BIOLOGICAL BINDING MOLECULES

(71) Applicant: AVA Lifescience GmbH, Denzlingen (DE)

(72) Inventors: Holger Klapproth, Freiburg i. Br. (DE); Marc A. Kessemeier, Emmendingen (DE); Ulrich Birsner, Freiburg i. Br. (DE)

( * ) Notice: Subject to any disclaimer, the term of this patent is extended or adjusted under 35 U.S.C. 154(b) by 1121 days.

(21) Appl. No.: 17/608,056

(22) PCT Filed: May 2, 2019

(86) PCT No.: PCT/EP2019/061308

§ 371 (c)(1),
(2) Date: Nov. 1, 2021

(87) PCT Pub. No.: WO2020/221466

PCT Pub. Date: Nov. 5, 2020

(65) Prior Publication Data

US 2022/0227864 A1 Jul. 21, 2022

(51) Int. Cl.
| | |
|---|---|
| *C07K 16/28* | (2006.01) |
| *C07K 16/30* | (2006.01) |

(52) U.S. Cl.
CPC ...... *C07K 16/2803* (2013.01); *C07K 16/3061* (2013.01); *C07K 2317/24* (2013.01)

(58) Field of Classification Search
None
See application file for complete search history.

(56) References Cited

U.S. PATENT DOCUMENTS

| | | | | |
|---|---|---|---|---|
| 7,927,817 | B2 | 4/2011 | Rother et al. | |
| 11,591,391 | B2 * | 2/2023 | Birsner ............ | A61K 39/39566 |
| 11,634,487 | B2 * | 4/2023 | Birsner ............ | G01N 33/57492 424/130.1 |
| 11,644,459 | B2 * | 5/2023 | Klapproth ........ | G01N 33/57484 435/7.24 |
| 11,981,735 | B2 * | 5/2024 | Duhren-Von Minden ................... C07K 16/2803 |

FOREIGN PATENT DOCUMENTS

| | | | |
|---|---|---|---|
| EP | 1001020 A1 | 5/2000 | |
| EP | 3424528 A1 * | 1/2019 | ....... A61K 39/39566 |
| WO | 2019079762 A1 | 4/2019 | |

OTHER PUBLICATIONS

Janeway, et al., Immunobiology: The Immune System in Health and Disease, 5th edition, 2001 (Year: 2001).*
Rudikoff, et al., PNAS, 1982, 79, p. 1979-1983 (Year: 1982).*
Lescar et al., J Biol Chem, 1995, 270, 18067-18076 (Year: 1995).*
Edwards, et al., J Mol Biol, 2003, 334, 103-118 (Year: 2003).*
Goel, et al., J Immunol, 2004, 173, 7358-7367 (Year: 2004).*
NIH-NCI, Cancer Prevention Overview, 2023 (Year: 2023).*
Mayo Clinic, Cancer Treatment, 2024 (Year: 2024).*
NCFR , Cancer Intervention vs Prevention: What does it Mean?, 2024 (Year: 2024).*
Giachino, et. al, (J Exp Med, 1995, 181, 1245-1250 (Year: 1995).*
Maity, et. al, PNAS, 2020, 117, 4320-4327_supplemental info (Year: 2020).*
Maity, et al., PNAS, 2020, 117, 4320-4327 (Year: 2020).*
Claudia Minici et al. "Distinct homotypic B-cell receptor interactions shape the 1-10 outcome of chronic lymphocytic leukaemia" Nature Communications, vol. 8. Jun. 9, 2017 (Jun. 9, 2017). p. 15746 DOI: 10.1038/ncomms15746XP055481551.
International Search Report, English Translation, PCT/EP2019/061308 Jan. 24, 2020 EPO Rijswijk, Netherlands.

* cited by examiner

*Primary Examiner* — Misook Yu
*Assistant Examiner* — Samantha Lake Hopkins
(74) *Attorney, Agent, or Firm* — SAFFIRE IP; Daren P Nicholson

(57) ABSTRACT

The invention relates to the field of the preparation, identification and selection of biological binding molecules such as antibodies or fragments thereof, and also the use thereof in the context of therapy and prophylaxis of cancers, such as malignant B-cell neoplasia in particular. The binding molecules are capable of selectively binding to B-cell receptors that have a light chain according to SEQ ID NO. 18.

9 Claims, 2 Drawing Sheets

Specification includes a Sequence Listing.

BIOLOGICAL BINDING MOLECULES

CROSS-REFERENCES TO RELATED APPLICATIONS

This application is a national stage application under 35 U.S.C. 371 and claims the benefit of PCT Application No. PCT/EP2019/061308 having an international filing date of May 2, 2019, which designated the United States, the contents of which is incorporated herein by reference in its entirety.

FIELD OF THE INVENTION

The present invention relates to the field of the production, identification and selection of antibodies or fragments thereof, and also the use thereof in the context of prophylaxis and therapy of cancers such as malignant B cell neoplasia, in particular, as well as the accompanying diagnosis.

SEQUENCE LISTING

The instant application contains a Sequence Listing, which has been submitted electronically in ASCII format in parent PCT/EP2019/061308 on May 2, 2019, and was uploaded from the International Bureau under the name eolf-seql.txt on Nov. 1, 2021, and is hereby incorporated by reference in its entirety. Said ASCII copy as uploaded from the International Bureau is 14,717 bytes in size.

BACKGROUND OF THE INVENTION

Malignant B cell neoplasia is generally defined as a malignant disease of the hematopoietic or lymphatic system. It includes diseases such as leukemia that are classified as cancers in a broader sense. Leukemias are characterized by a strongly increased formation of non-functional precursor cells of the white blood cells, also referred to as leukemia cells. These cells spread in the bone marrow, suppress the normal hematopoiesis there and usually accumulate in the peripheral blood in large numbers. They can infiltrate the liver, spleen, lymph nodes and other organs and thus impair their function. The disruption of hematopoiesis leads to a decrease in normal blood components, which may result in anemia due to a lack of oxygen-carrying red blood cells, a lack of hemostatic platelets, and a lack of mature functional white blood cells.

Depending on the course of the disease, a distinction is made between acute and chronic leukemia. Acute leukemia is a life-threatening disease that, if left untreated, can lead to death in a matter of weeks or months. Chronic leukemia, on the other hand, usually runs its course over several years and is often asymptomatic in the early stages.

The most important forms of leukemia are:
acute myeloid leukemia (AML)
chronic myeloid leukemia (CML)
acute lymphatic leukemia (ALL)
chronic lymphatic leukemia (CLL)

Usually, leukemias are treated in the context of chemotherapy. Newer forms of therapy increasingly rely on the use of monoclonal antibodies such as GA101 (obinutuzumab), which acts as a CD20 antibody similar to rituximab and ofatumumab and is used to treat chronic lymphatic leukemia (CLL). By using these antibodies, the remission-free time can be extended by approximately 10 months.

Other malignancies of the hematopoietic or lymphatic system (malignant B cell neoplasia) include lymphomas such as Hodgkin's lymphoma and the B cell variants of non-Hodgkin's lymphomas.

If antibodies are generated against receptors, animals are usually immunized with the receptor (purified, cloned, or as peptide fragments) and hybridoma cells are generated. These hybridoma cells produce antibodies, which are then tested by ELISA or by expressed receptors in cell systems. For this purpose, established cell lines are used, since only these can be easily cultivated. Antibodies can be generated in the process that bind relatively specifically to a certain receptor type (e.g. anti-IgG1, anti-IgE). However, this often leads to cross-reactions with other receptors or other epitopes.

For a diagnostic or therapeutic application of BCR antibodies, it is usually not sufficient to use only one antibody against the BCR in general, since such a broad-spectrum application can lead to false positive results or cause considerable side effects. Rather, it would be desirable to provide an antibody that selectively binds to a receptor that has a light chain with epitope VL3-21 according to SEQ ID NO. 18. This light-chain epitope is overrepresented in neoplastic B cells. Such an antibody is not known in the prior art and a method for its production or obtaining it by selection does not exist.

Therapies in the prior art for the treatment of leukemias are very stressful for the patient. In general, it can be summarized that the undesirable side effects of the therapy and the often insufficient effect of the drugs lead to a high death rate of this disease, because not only tumor cells but also healthy cells of the immune system are damaged. In addition, often there is no cure, but only the creation of a certain period in which the disease is remission-free. Therefore, it is important for the identification and selection of patients to be treated, as well as for the creation of an individual therapy plan, to have available diagnostic tools and diagnostic methods using them, with which certain forms of malignant B cell neoplasms can be differentially detected.

BRIEF SUMMARY OF THE INVENTION

Therefore, the object of the present invention is to provide alternative concepts and active agents, such as in particular alternative antibodies for diagnostic, prophylactic and/or therapeutic use, which overcome the existing problems of the prior art. Preferably, the present invention is also intended to provide evidence for the presence of suitable surface structures for therapeutic use of the antibody ("companion diagnostics").

Vector with HC/LC (VL3-21) typical of CLL subset 2 (see FIG. 1B).

Vector with a non-CLL subset 2 HC/LC typical for CLL subset 2 (VL3-21; without target motif R110G) (see FIG. 1C)

Vector with a HC typical for CLL subset 2/a non-CLL subset 2 LC (see FIG. 1D)

Vector with a non-CLL subset 2 HC/a non-CLL subset 2 LC (see FIG. 1E)

Vector with HC/LC typical for CLL subset 2 (VL3-21; including mutation R110G (target motif)) (see FIG. 1F).

Figure 2:
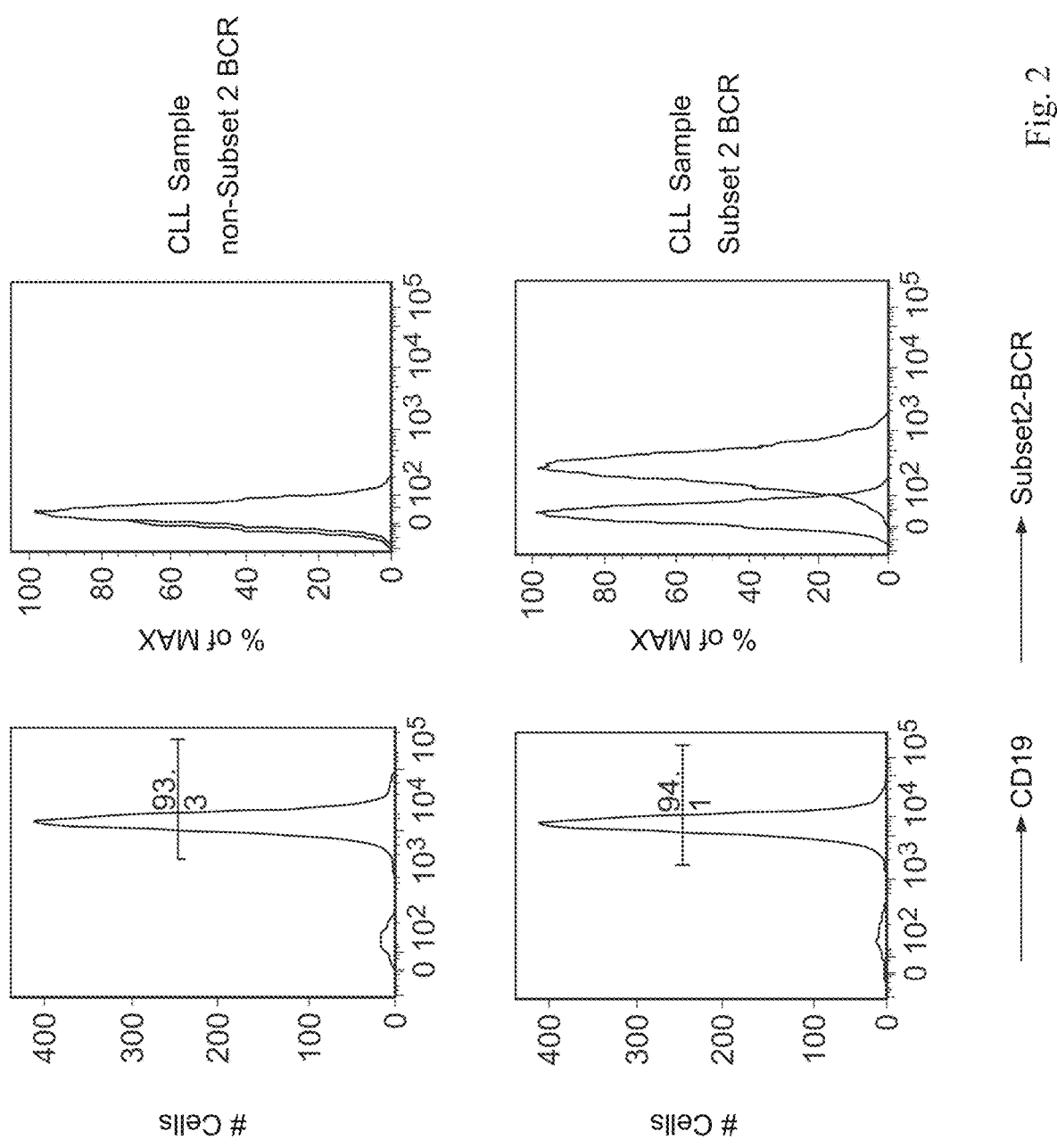

FIG. 2 shows an example of a FACS analysis performed on a BDCalibur using the VL3-21 specific antibody. In a first step, the CD19 positive B cells were selected for further analysis (left panel). These were then analyzed for binding of the specific antibody (right panel).

DETAILED DESCRIPTION OF THE INVENTION

Before the individual aspects of the present invention are discussed in detail, a clarification of relevant terms used in the context of the present description is provided.

The term "neoplasia" as used herein generally refers to a new formation of body tissue. If this is a pathological or malignant manifestation, it is referred to as a malignant neoplasia. Thus, a malignant B cell neoplasia is a malignant and uncontrolled new tissue formation of B cells, and this term applies equally to all B cell associated cancers such as leukemias and B cell lymphomas.

An "area to kill neoplasia" may kill neoplasia either as a result of a direct or indirect effect. In the case of therapeutic use of specific antibodies, a molecule is bound to the antibody or to a functional fragment of that antibody, or to another biological binding molecule comprising that antibody or its fragment, so as to exert an effect beyond the effect of binding the antibody or its fragment. Such a molecule may be selected, for example, from the group consisting of an immunotoxin, a cytokine, a chelator, a radioisotope, and combinations thereof.

In this case, "biological binding molecules" means, for example, but not exclusively, antibodies including fusion proteins. Advantageously, and therefore preferably, such an antibody is selected from the group consisting of an IgG antibody, an IgM antibody, a humanized IgG antibody, and a human antibody in which the recognition sequence of the epitope is inserted. Such a binding molecule may also be provided in the form of a functional fragment of the entire antibody, e.g., as a Fab fragment. A binding molecule may also comprise other domains that, for example, lead to the killing/death of neoplasia and accordingly have the functionality of an immunotoxin and/or immunocytokine. In particular, such a binding molecule may also be membrane- or cell-bound. One such membrane-bound form of a binding molecule is, for example, the chimeric antigen receptor ("CAR") on CAR-T cells.

Furthermore, a binding molecule may also include other domains or additional entities whose use is advantageous in the context of diagnostic applications. Using flow cytometry, these can be fluorescent dyes (e.g., FITC, R-phycoerythrin (R-PE), allophycocyanin (APC)) or biotin as well as other substances known to the person skilled in the art. Furthermore, a binding molecule can also be used together with substrate-substituting enzymes (e.g., HRP) in the context of immunohistochemical procedures. Furthermore, fusion proteins can also be provided for diagnostic purposes, in which fluorescence proteins such as the green fluorescence protein (GFP) are coupled to the FC part of the antibody for detection.

The task of the B cell receptor complex (BCR) on the surface of a B cell is to recognize and bind pathogens. This binding leads to a conformational change of the BCR, triggering a signaling cascade that ultimately leads to B cell activation. The BCR is produced in great diversity in maturing B cells.

In humans and also in some other mammals, B cell development takes place in the bone marrow and fetal liver, respectively. The developing lymphocytes receive the signals necessary for the developmental program from so-called stromal cells. In B cell development, the formation of a functioning B cell receptor (the membrane-bound form of 'antibody') is crucial. Only with this antigen receptor are mature B cells later able to recognize foreign antigens and bind to hostile structures by forming appropriate antibodies. The antigen specificity of the receptor is determined by the linkage of certain gene segments. The segments are called V, D and J segments, which is why the process is called V (D) J recombination. In this process, these segments, which form the antigen-binding part of the B cell receptor, are rearranged. The entire receptor consists of two identical light protein chains and two identical heavy protein chains, with the heavy chains linked to the light chains by disulfide bridges, respectively.

Each of the light chains consists of one variable and one constant domain, where the variable domain determines antigen recognition, whereas the constant domain determines the five immunoglobulin classes or is responsible for membrane anchoring in the T cell receptor. The light chain is constructed by somatic recombination from a pool of V and J genes and the constant chain lambda or kappa. The heavy chain involves three components that build the variable part (V, D, J). While especially the heavy chain has been the main focus of research so far and has been very well studied, little attention has been paid to the light chain thus far. Of the light chain, 2 gene loci are known, namely a locus for kappa with 40 V gene segments, and a locus for lambda with 30 V gene segments. In CLL, certain combinations are predominant on corresponding B cells (Stamatopoulus et al 2005 (BLOOD Vol 106, Number 10)). In particular, analysis of B cells from CLL patients showed that the cells of a surprisingly high number of patients with autonomously active BCRs have the V chain VL3-21. It is known that the V chain VL3-21 occurs in three variants, these variants differing from each other by a maximum of two amino acids and can be used with the same effect with respect to the present invention.

The large repertoire of immunoglobulins and T cell receptor specificities, which would exceed the size of the genome if a separate gene were available for each molecule, is realized, among other things, by the fact that the individual gene segments (V, D, J) are available in several copies prior to rearrangement, which can be randomly combined with each other in the manner of a combination lock during the maturation of the lymphocytes.

In VDJ recombination, the V, D and J segments of the B cell receptor heavy chain are linked first, followed by the V and J segments of the receptor light chain. Only if the genes are successfully rearranged, which is called productive gene rearrangement, can the cell proceed to the next developmental step.

B cells that react to the body's own antigens during their maturation in the bone marrow die in most cases by apoptosis. In the blood of healthy people, small amounts of autoreactive cells can be detected, among others against thyroglobulin or collagen (Abul K. Abbas: *Diseases of Immunity* in Vinay Kumar, Abul K. Abbas, Nelson Fausto: *Robbins and Cotran—Pathologic Basis of Disease*. 7th ed. Philadelphia 2005, p. 224 f.)

Since the process of generating such a BCR is based on a random assembly of gene segments, it can happen that the newly formed BCR recognizes unwanted body structures and thus becomes "permanently activated." In order to prevent the development of such a "permanently active or activated" BCR, various body-own protective mechanisms exist. However, if these are overcome due to a pathological change in the developing B cell, a malignant or autoimmune manifesting disease may develop.

In contrast, an "autonomously active" or "autonomously activated" BCR is a special type of permanently active BCR. While conventional activation originates from an external antigen (see above), the autonomously active BCR results from its interaction with membrane structures on the surface of the same cell. For the clinical picture of CLL, an interaction triggering autonomous activation could be shown between BCRs that were adjacent to each other on the surface of the same cell (M. Dühren-von Minden et. al: Nature 2012). Another example of an autonomously active BCR is represented by the pre-BCR, which is expressed during the development of a B cell as a developmental check. However, in addition to the interaction of neighboring receptors (BCR:BCR), an interaction between a receptor and a membrane protein (BCR: membrane protein) can also lead to an autonomously active or activated BCR.

The solution to these problems according to the invention is based on the surprising finding that receptors that are autonomously active or autonomously activated are present on the tumor cells of patients with CLL, and that these autonomously active or activated receptors are characterized by the presence of common epitopes that cannot be detected in corresponding receptors of healthy cells of the same patient. These cells can thus be specifically recognized and treated by an antibody due to the presence of autonomously active B cell receptors characterized by the presence of the aforementioned epitopes, such that healthy B cells lacking these characteristics are not thereby affected, allowing treatment to be carried out in a much more specific manner and with fewer undesirable side effects.

However, in the course of the numerous experiments conducted for the present invention, it was surprisingly found that antibodies with particular specificity for these modified receptor domains (epitopes) cannot be produced and selected by common standard methods. Only after the experimental conditions were adapted in such a way that genetically modified cells, whose modified B cell receptors were in a native and activated state, were used in binding studies, could suitable antibodies with the desired and required specificity be obtained. In other words, it is essential for the solutions proposed according to the invention that the cells used in binding studies to select suitable diagnostic, prophylactic or therapeutic antibodies present their modified domains (epitopes) in a largely native and activated form. In this context, it turned out that so-called pro-/pre-B cells are particularly suitable due to their physiological constitution. The provision of such specific antibodies and functional fragments thereof, which also possess this specific binding behavior, thus enables tumor-specific diagnosis and treatment, which is characterized by a significantly improved treatment success and, thanks to the reduction of undesired systemic effects, a significantly increased therapeutic success.

As mentioned above, biological binding molecules in the form of antibodies or functional fragments thereof and a method for the production (identification and selection) of such binding molecules are provided, which selectively bind to B cells having B cell receptors with epitope VL3-21 as well as mostly also to the modified epitopes of autonomously active membranous immunoglobulins of B cell neoplasia. Furthermore, diagnostic, prophylactic, as well as therapeutic methods using such binding molecules are proposed, whereby the therapeutic application refers to the inhibition of growth or killing of cells expressing such membranous immunoglobulins of this type. Diagnostic methods mainly refer to the in vitro detection of this receptor subtype which is characterized by the presence of VL3-21 on the light chain of BCRs on B cells, in particular in the context of a therapeutic decision to use the proposed antibody ("companion diagnostics").

In general, leukemias and lymphomas represent attractive targets for the treatment with immunotoxins and/or immunocytokines. The response of patients with B cell malignancies has been extensively studied in phase I/II clinical trials of immunotoxin activity (Amlot et al., (1993), Blood 82, 2624-2633; Sausville et al., (1995), Blood 85, 3457-3465; Grossbard et al., (1993), Blood 81, 2263-2271; Grossbard et al., (1993) Clin. Oncol. 11, 726-737). To date, some antitumor responses have been noted, but immunotoxin-mediated toxicity to normal tissue often prevented dose escalations to therapeutic levels. Several B cell-specific antigens, such as CD19, CD22, and CD40, have been selected as targets of immunotoxins generated with plant toxins, such as ricin A chain, and bacterial toxins, such as *Pseudomonas* exotoxin A (PE) (Uckun et al., (1992), Blood 79, 2201-2214; Ghetie et al., (1991), Cancer Res. 51, 5876-5880; Francisco et al, (1995), Cancer Res. 55, 3099-3104).

Membranous immunoglobulins represent well-suited targets for targeted, i.e. specific, immunotherapy. During B cell development in the bone marrow, each individual B cell progenitor generates its own and nearly unique B cell receptor (BCR) by rearranging single gene segments.

Two variants (subset 2; subset 4) of the autonomously active BCR are known that differ from each other with respect to their respective characterizing molecular motifs (epitopes) (Minici, C. et al., Distinct homotypic B cell receptor interactions shape the outcome of chronic lymphocytic leukemia, Nature Comm. (2017)). Both variants have different short amino acid sequences that are specific to each of these variants. It is known to the person skilled in the art that other CLL B cell receptors are autonomously active in addition to the listed subsets. The region of subset 2 relevant for the autonomously active functionality of the receptor is characterized by the amino acid sequences KLTVLRQPKA (SEQ ID NO. 1) and VAPGKTAR (SEQ ID NO. 2) of the light chain, whereas the region of subset 4 relevant for the autonomously active functionality of the receptor is defined by the amino acid sequences PTIRRYYYG (SEQ ID NO. 3) and NHKPSNTKV (SEQ ID NO. 4) of the variable part of the heavy chain. The sequences used to generate the murine antibodies in the immunization process for subsets 2 and 4 are described in SEQ ID NOS. 5 and 6 (vHC; LC) and 7 and 8 (vHC; LC), respectively. For completeness, another target sequence or epitope with specificity for the variable part of the heavy chain of a BCR of subset 4 is given in SEQ ID NO. 17 (VSSASTKG). In addition to the target sequences (epitopes) responsible for the formation of the autonomously active state of the BCR (subset 4) according to SEQ ID NOS. 3 and 4, the sequence according to SEQ ID NO. 17 thus represents a further property characteristic for this subset.

It should be noted that the finding and characterization of subsets 2 and 4 as two variants of the B cell receptor in patients with critical disease progression is based on the investigation of numerous individual case studies and therefore does not imply that the same target sequences (epitopes) characteristic of the two known subtypes are not present in a possible multitude of other subtypes of the BCR and correlate with severe disease progression.

It should be noted that the present discussion in connection with the finding of binding molecules specific for BCRs of subtypes 2 and 4 is to be understood as preliminary work that has led to the finding of the further binding molecule specific for epitope VL3-21 according to the invention and is itself the subject of parallel patent applications.

Although antibodies against both of these subsets should in principle be able to be generated using standard methods, e.g. in mice, it was surprisingly observed that immunization using peptides did not lead to the formation of the desired specific antibodies. Immunization using individual chains of the receptor, such as the use of the light chain of BCR comprising the modified sequence regions, also did not produce the desired success, which is why mice were ultimately immunized with the recombinantly produced soluble form of BCR (cf. SEQ ID NOS. 5 and 6). Immune cells with the desired specificity were subsequently obtained from these mice and transformed into hybridoma cells by cell fusion. Surprisingly, the active antibodies could not be identified by means of the ELISA test or other standard methods. However, the clones identified as potential binding partners in a first step by ELISA proved after selection to be either non-specific binding or not binding to the autonomously active receptor (including SEQ ID NOS. 1 and 2) and therefore had to be discarded.

The methods used until this finding included not only standard methods such as ELISA and SPR, but also intracellular expression in fibroblasts with intracellular FACS staining as a binding control.

After elaborate further series of experiments, it was shown that successful selection of binding molecules suitable according to the invention can neither be performed with free receptors or their fragments nor with membranous or intracellular receptor fragments. Instead, it was observed that the selection was only successful using a cell system in which the complete and functional B-cell receptor was presented in a membranous manner. It is of great importance that the BCR with its modified regions (epitopes) is autonomously actively available or presented in or on these cells. Only with this approach, the conditions of which reflect a largely physiological-native in situ scenario, was it possible to identify an antibody that binds highly specifically and selectively only to tumor cells, i.e. to B cells expressing a BCR with an epitope on their cell membrane characteristic of subset-2 or subset-4 of this cell type, but not to other B cells or their receptors (BCRs), which by definition do not represent subset-2 or subset-4 B cells. In other words, these binding molecules bind selectively to autonomously active or autonomously activated B cell receptors characterized by the presence of structural domains or epitopes (target sequences) and causative for the autonomously active or activated state of the B cell receptors.

It was further shown that the use of arrested pro-/pre-B cells obtained from "triple knockout" (TKO) mice are particularly well suited to express these receptors and to be used in the context of a test system for the identification of these receptors, despite the difficulty of handling and the effort required to obtain them. The stage of pro-/pre-B cells is naturally designed to carry out the maturation and selection of BCRs, and the cells of this stage are particularly suitable, due to their enzyme equipment (chaperones, etc.), to fold even "difficult" BCR components correctly and to present them on their surface in a sufficiently physiologically native form. The deletions (knockouts) described below prevent recombination or the use of the surrogate light chain from altering the desired BCR. By using these cells or this cell type of arrested pro-/pre-B cells for the expression and presentation of BCRs in the context of a selection of antibodies with selective-specific binding behavior towards autonomously active or activated B cell receptors, a selection platform is provided that is characterized by a much higher quality compared to the systems conventionally used for selection in the prior art, which justifies the high effort of using primary TKO cells, or their cultivation over a few passages.

After the previously described selection of suitable hybridoma cells, antibodies suitable for diagnostic, prophylactic and/or therapeutic purposes could be obtained in larger quantities in the form of monoclonal antibodies. By sequencing the DNA of these cells, the binding site of the antibody could be determined (cf. SEQ ID NOS. 9 and 10). Corresponding methods are known to the person skilled in the art and are also commercially available. Here, it is advantageous to obtain a larger number of hybridoma cells and to select those with the best binding activity (specificity and binding strength/affinity).

The genetic information about the binding site thus obtained was used to insert the sequence coding for it into an expression plasmid containing the DNA of a human antibody sequence to generate a humanized monoclonal antibody with the desired specificity by the usual route of recombination. These humanized antibodies, due to their unique specificity, showed better diagnostic specificity or prophylactic and therapeutic efficacy with comparatively very low side effects compared to conventional diagnostic agents and active substances. It is clear to the person skilled in the art that these humanized antibodies can be produced in large quantities by biotechnological means. For purification of the synthesized antibodies, standardized methods can be used, such as combinations of precipitation, filtration and chromatography, which are sufficiently known to the person skilled in the art, whereby care should be taken not to denature the antibodies and to quantitatively remove possible foreign substances such as proteins, pyrogens and toxins.

Preferably, the desired antibodies are expressed in systems in which the antibody undergoes glycosylation such as, in particular, human glycosylation. Such systems are sufficiently known to the person skilled in the art and include the use of insect cells (S2 cells), mammalian cells (CHO cells) and, particularly preferably, human cells such as HEK293T cells.

The sufficiently purified antibody may in itself be therapeutically effective, provided it has an isotype that elicits a specific immune response, such as an IgG subtype that leads to an immune response against the tumor via Fc receptors.

However, the antibody may also be present as a fragment. In this case, it is important that the antigen-binding site is present in the fragment, i.e. that it is a functional fragment. Such fragments can be produced, for example, by protease treatment as F (ab) fragments. Since these fragments are truncated in the constant part of the antibody, it is advantageous and therefore preferred here to insert an effector molecule for killing neoplasia.

According to an alternatively preferred embodiment, the antibody is provided with a conjugate to enhance its effect. This conjugate is a neoplasia killing region and can kill such neoplasia either as a direct or indirect effect. An example of such a conjugate is the binding of ricin to the antibody, where its preferential covalent binding is performed, for example, by using chemical crosslinkers. Such molecules and methods are described extensively in the book Bioconjugate Techniques by Greg T. Hermanson in Chapter 11: Immunotoxin Conjugation Techniques.

According to a further preferred embodiment, the antibody may also be present in modified form such as a biological binding molecule in the form of a fusion protein with T cell-specific activation domains. To generate this so-called chimeric antigen receptor (CAR), T cells are first obtained from the patient's peripheral blood and genetically modified in vitro so that they express the CAR on their cell surface. Subsequently, these modified T cells are reintroduced into the patient, thus making CAR T cell immunotherapy feasible (see, e.g., N Engl J Med. 2014 Oct. 16; 371 (16):1507-17. doi: 10.1056/NEJMoa1407222).

For therapeutic use, the antibody is preferably used in a composition comprising a pharmaceutically acceptable carrier.

A pharmaceutically acceptable carrier is a carrier that is physiologically acceptable to a treated patient and preserves the therapeutic properties of the compound with which it is administered. An exemplary pharmaceutically acceptable carrier is physiological saline. Other suitable physiologically acceptable carriers and formulations thereof are known to the person skilled in the art and are described, for example, in Remington's Pharmaceutical Sciences (18th Ed.), publisher A. Gennaro, 1990, Mack Publishing Company, Easton, PA).

Another possible therapeutic application of the binding molecules according to the invention is the method of apheresis, which is known per se and involves treatment of the blood or a blood sample of a patient outside his body in the sense of "blood washing."

For example, the antibody according to the invention can be used in an apheresis system to separate leukemia cells from a patient's blood sample. Various methods are suitable for this purpose in principle, as is known to the person skilled in the art.

According to a first embodiment, the antibodies may be bound to magnetizable particles (beads) (e.g., dynabeads). The blood is provided with an anticoagulant and brought into contact with the particles outside the patient's body. Ideally, at least one particle, preferably 10 to 100 particles, is used for this purpose per tumor cell. A particle with a size of less than 20 μm, for example, typically contains several antibodies of the same specificity (number of particles greater than 5000/μl blood). Magnets can then be used to bind these particles before the purified, remaining blood is returned to the patient. This therapeutic measure significantly reduces the number of tumor cells in the patient's blood. According to another embodiment, the particles have sizes greater than 20 μm and also have a large number of antibodies per particle (>100, >1000). Thus, many lymphocytes (tumor cells) can be bound and removed with one particle. These particle/cell conjugates are removed by classical centrifugation as commonly used in apheresis. The times required for this depend on the type of particles and apparatus and must be determined experimentally.

In another embodiment, both the particle/cell conjugates (especially when using large particles over 20 μm in diameter) and free particles without cell binding can be separated from blood using a fine network. Such networks are commercially available, for example, as so-called 'cell strainers.' Methods for conjugating the antibodies to the particles are sufficiently known to the person skilled in the art. Procedural instructions are provided e.g. by the Dynal company to its customers.

For diagnostic use, the antibody is preferably used in standardized procedures such as flow cytometry or immunohistochemistry. Preferably, the antibodies, biological binding molecules or functional fragments thereof proposed for diagnostic purposes have a murine backbone. Detection in the flow cytometer is preferably by means of secondary antibodies, or alternatively preferably by means of fluorescent dyes directly bound to the antibodies, biological binding molecules or functional fragments thereof.

For stable storage, it may be advantageous to provide the antibody or fragments thereof in a stabilized form, which is accordingly also preferred. For this purpose, drying with a stabilizing salt buffer can be carried out, for example. Such a buffer may be, for example, a phosphate-buffered salt solution (PBS), as is known to the person skilled in the art. A suitable form of drying is, for example, freeze-drying or lyophilization.

Individual aspects of the present invention are explained in more detail below by means of examples.

Before detailed explanations of the experimental procedure are presented, reference is made to the following.

The generation and identification of antibodies that selectively bind to the modified B-cell receptors were characterized by major and unforeseen problems. Hybridomas were generated by standard methods. Supernatant from the hybridoma groups was pooled and assayed for positive binding events by ELISA (soluble B-cell receptors on the ELISA plate). Positive pools were singulated and the individual clones tested. Surprisingly, no more positive clones were identified by ELISA. The positive pool ELISA signals subsequently turned out to be non-specific binding.

To create better epitopes for antibody recognition, the BCR light chain was now expressed in fibroblasts. This should ensure proper folding of the protein carrying the motif (epitope) responsible for autonomous signaling. Intracellular FACS analyses were performed with these cells. No positive clone (antibody) could be identified.

For this reason, in another experiment, RAMOS cells (human Burkitt lymphoma cell line) were modified to exhibit functionally modified BCRs. This was to ensure completely correct biosynthesis, folding and modification of the BCR. To do this, the cell's own BCR was deleted using CRISPR and then the "CLL receptor" was reconstituted using molecular biology (electroporation of CMV vectors). These cells were used to test positive binding events. Again, no positive clone was detectable by FACS.

In contrast, surprisingly, the use of murine TKO ('triple knock-out') cells (arrested pro-/pre-B cells), into which the CLL receptor was introduced using a gene shuttle, yielded a positive clone. This is despite the fact that the human cell system could not ensure this. These cells have the following three knockouts in their genome as a special feature:
  the knockout of RAG2 prevents somatic recombination of its own immunoglobulin heavy and light chains, thus excluding endogenous formation of a BCR. This leads to arrest, blockage or "freezing" of appropriately treated B cells at this stage of development. It is known that RAG1 and RAG2 form a complex that makes the usual VDJ rearrangement possible in the first place, which is why knockout of RAG1 is an equally effective agent and thus an alternative to knockout of RAG2 and is encompassed by the teachings of the invention.

deletion of lambda5, part of the surrogate light chain, prevents the formation of a pre-BCR. Since the pre-BCR is autonomously active, this would interfere with the detection of an autonomously active receptor. Since a new BCR is cloned into the cell here, a pre-BCR is undesirable because it would appear on the surface with the desired heavy chain (HC) in association with the undesired surrogate light chain and interfere with selection.

knockout of SLP65, an adaptor protein of central importance in the BCR signaling pathway, prevents activation of the TKO cell by a possibly reconstituted BCR.

The combination of knockouts of RAG2 or RAG1 and lambda5 results in a blockade in the transition from the pro-B cell stage to the pre-B cell stage, which is classically characterized with the onset of rearrangement of the heavy chain (HC) VDJ segments. Therefore, these are pro-/pre-B cells.

Knockout of RAG2 or RAG1 and lambda5 is sufficient for BCR expression and selection of the appropriate antibody. Reconstitution with inducible SLP65 can be used to measure the activity of the BCR.

The method of choice here is to measure Ca-flux after induction of SLP65 by FACS analysis and the use of a $Ca^{2+}$ dependent dye such as Indo-1. These methods are well known to the person skilled in the art (see (M. Dühren-von Minden et al.; Nature 2012).

The first two knockouts ensured that only the "BCR of interest" was expressed on the surface. Moreover, by using an inducible SLP65 with which the cells were reconstituted, the function of the expressed BCRs can be characterized and thus the autonomously active state of the BCRs on the surface can be verified before selection.

BCR expression was determined using anti-IgM and anti-LC antibodies on FACS. For this purpose, some cells were taken and stained with 5 μl of antibody each in a total volume of 100 μl in PBS.

Using these cells as a "target," it was now possible by FACS to identify an antibody that specifically binds to the modified region by which the autonomous activation of the BCR is established and characterized. And this, although binding to the same receptor type in RAMOS cells was not successful!

Figure 1:
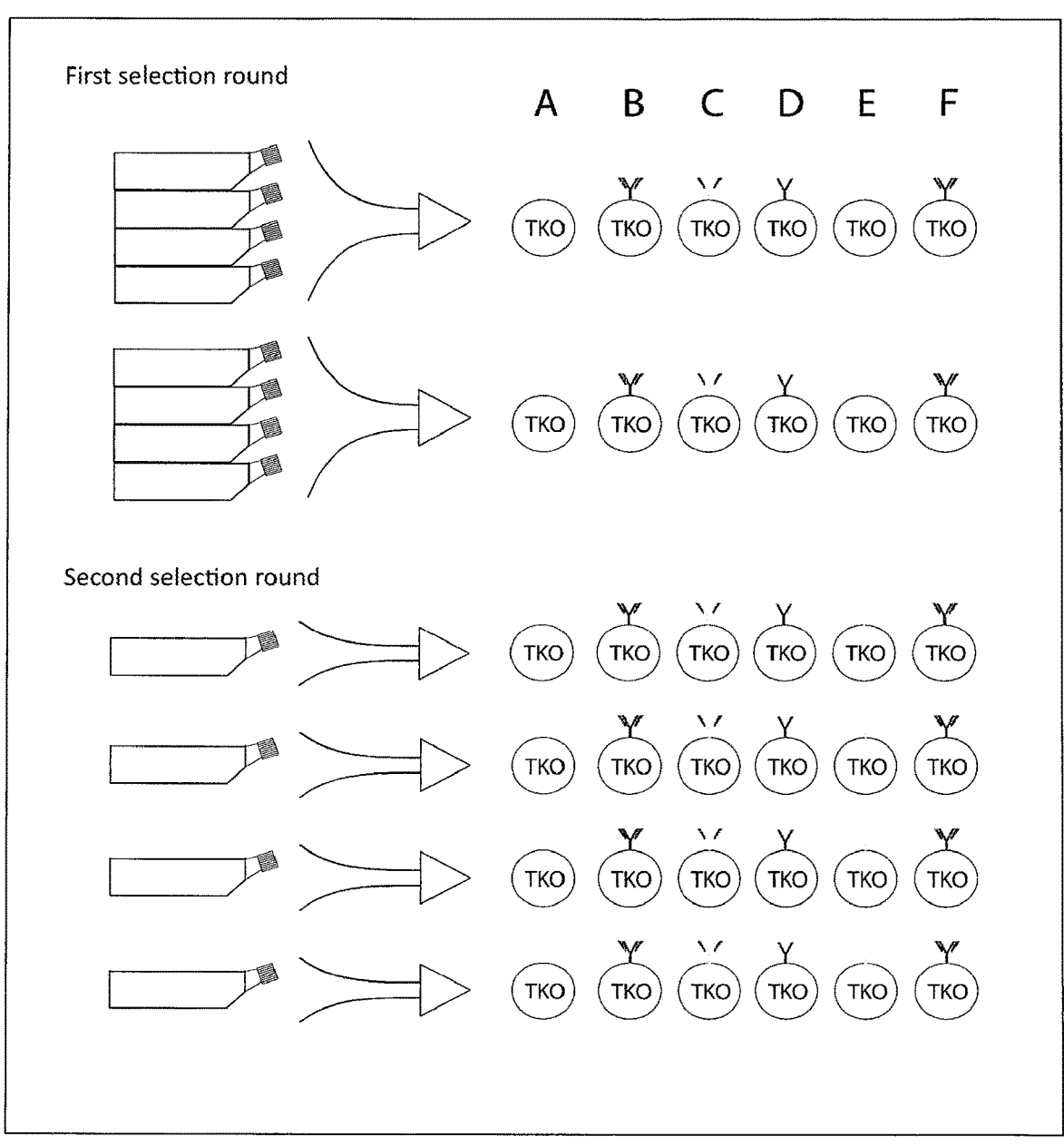
FIG. 1 schematically illustrates selection of a CLL subset 2 BCR used to identify and select positive antibody clones that selectively bind to B cells having B cell receptors with epitope VL3-21 as well as mostly also to modified epitopes of autonomously active membranous immunoglobulins of B cell neoplasia. For the screening procedure, different vectors for the following heavy chain (HC) and light chain (LC) combinations of the corresponding CLL-BCRs were used in a previous transformation, and these combinations were used on the surface of the BCR reconstitution system:
Control (transformation vector without BCR) (see FIG. 1A).

For this purpose, cells carrying the "BCR of interest" on the surface were first incubated with the pooled supernatants, and after some washing steps, the bound antibodies were detected using secondary antibodies. For specific selection, TKO cells (TKOs) expressing different versions of the "BCR of Interest" were used. The selection matrix shown in FIG. 1 is exemplary for the selection of a CLL subset 2 BCR and was used to identify and select positive clones. For ease of identification, the supernatants of the hybridomas were pooled and measured. The groups that showed binding were singulated, and the supernatants of the respective hybridomas were tested for binding.

Confirmation that the selected antibody binds specifically to the modified BCR and not to other BCR variants was performed using two blank samples, i.e., cells without BCR (see FIG. 1A) and cells with non-CLL BCR (see FIG. 1E). Primary B cells from the blood of leukemia patients were analyzed for binding by FACS. The selected antibody was able to specifically identify those BCRs that had the target structure. This was confirmed at the genomic level. Samples without this target structure did not show binding.

In the course of the investigations, it was found that all autonomously active cells of the type CLL subset 2 used, in addition to a specific mutation (R110G), also had a specific variant of the V region of the BCR light chain. This epitope variant was identified as VL3-21 (SEQ ID NO 18) and forms the subject of the present invention. It has been shown that this epitope is present on the BCR of tumor cells in approximately 30% of all CLL cases. However, this epitope can also be present on healthy cells. Thus, this is a tumor-associated epitope that can be used to diagnose and treat the tumor. This is especially true since there are a large number of variants of this V domain, so that the variant VL3-21 described here is expressed by less than 5% of the cells in "healthy," i.e. non-tumor B cells. Thus, there is the therapeutic possibility of a priority attack on neoplastic B cells (tumor cells) with a much lower impairment of healthy, non-tumor B cells compared to the conventional use of non-specific antibodies against the BCR. Therefore, the proposed antibody or a functional fragment thereof with specificity for VL3-21 can be used to provide a much more specific and less stressful therapy for the patient. In addition, the antibody against VL3-21 can be used for so-called companion diagnostics in e.g. CLL patients. In the context of this diagnostics, it is proven that the target structure VL3-21 of the therapeutic antibody is present on the tumor cells and justifies a relevant treatment with good chances of success.

The invention is explained in more detail below by means of examples in consideration of the figures.

Example 1

The starting point for the production of triple knockout cells (TKO) are transgenic mice, which have a respective knockout for the genes Lambda5, RAG2 and SLP65 (Dühren von Minden et al., 2012, Nature 489, pp. 309-313). The creation of such mice is known to the person skilled in the art and belongs to the prior art. To obtain the cells, the bone marrow of the femurs was extracted from the mice after they were killed. The cells thus obtained were then taken into culture under conditions conducive to pro/pre B cell survival (37° C., 7.5% CO2, Iscoves medium, 10% FCS, P/S, murine IL7). After several passages, FACS sorting was performed as a control, and the pro/pre B cells were sorted and then re-cultured. The markers used for this purpose are known to the person skilled in the art.

For reconstitution with a 'BCR of interest,' the corresponding heavy (HC) and light (LC) chain coding sequences were synthesized and then each cloned into expression vectors containing a CMV promoter. These were introduced into the packaging cell line (Phoenix cell line) by lipofection. After incubation for 36 hours, the virus supernatant was collected and used for spin infection of the TKO cells. Both the supernatant collection work and spin infection of the TKO are widely known procedures and are known to the person skilled in the art.

The structural features of subset-2 B-cell receptors were taken from the relevant literature (see above). Exemplary CLL subset 2 VH and complete LC DNA segments were synthesized by a contract manufacturer using a standard procedure. These were then fused to a murine IgG1 constant segment by PCR and cloned into a CMV vector. The sequence of the final vector was confirmed by Sanger sequencing.

```
CLL subset 2 VH (SEQ ID NO. 5):
EVQLVESGGGLVKPGGSLRLSCAASGFTFRSYSMNWVRQAPGKGLEW

VSSIISSSSYIYYADSVKGRETISRDNAKNSLYLQMNSLRAEDTALY

YCARDQNAMDVWGQGTTVTVSS

CLL-Subset 2 LC (SEQ ID NO. 6):
SYELTQPPSVSVAPGKTARITCAGNNIGSKSVHWYQQKPGQAPVLVI

YYDSDRPSGIPERFSGSNSGNTATLTISRVEAGDEADYYCQVWDSGS

DHPWVFGGGTKLTVLRQPKAAPSVTLFPPSSEELQANKATLVCLISD

FYPGAVTVAWKADSSPVKAGVETTTPSKQSNNKYAASSYLSLTPEQW

KSHRSYSCQVTHEGSTVEKTVAPTECS
```

A human cellular expression system based on HEK293T cells was used for CLL subset 2 IgG1 expression. A poly-ethylenimine (PEI)-based protocol was used for transfection. After several passages, the supernatant was pooled, and the medium contained in the combined cell supernatant was purified using protein G columns. The purity and quality of soluble subset-2 IgG1 was determined by Western blot.

Monoclonal antibodies were produced according to the standard procedure in mice and subsequent generation of hybridoma cells. Screening for positive clones was not performed by ELISA as conventionally. Since the target structure is a membranous receptor, it is of central importance to validate the binding of the potential antibodies also in a cellular system, i.e., largely preserving the cell physiological states native to this cell type. Groups of pooled supernatants were first examined for binding events by FACS analysis. For this purpose, different CLL subset 2 BCR variants were expressed on the surface of a cell line (TKO), which itself cannot express BCR. Thus, first the supernatants whose antibodies showed binding could be identified. Subsequently, the supernatants of the individual hybridoma clones were examined in more detail with regard to their binding in order to identify highly specific clones with high affinity in this way.

For the screening procedure, different vectors for the following heavy chain (HC) and light chain (LC) combinations of the corresponding CLL-BCRs were used in the previous transformation, and these combinations were used on the surface of the BCR reconstitution system:

Control (transformation vector without BCR) (see FIG. 1A).

Vector with HC/LC (VL3-21) typical of CLL subset 2 (see FIG. 1B).

Vector with a non-CLL subset 2 HC/LC typical for CLL subset 2 (VL3-21; without target motif R110G) (see FIG. 1C)

Vector with a HC typical for CLL subset 2/a non-CLL subset 2 LC (see FIG. 1D)

Vector with a non-CLL subset 2 HC/a non-CLL subset 2 LC (see FIG. 1E)

Vector with HC/LC typical for CLL subset 2 (VL3-21; including mutation R110G (target motif)) (see FIG. 1F).

This approach to selection is schematically illustrated in FIG. 1 using CLL subset 2 BCRs as an example, where the designation 'TKO' refers to TKO cells (see above).

In the first round of selection, supernatants from multiple clones were combined and examined with respect to their binding profile to the selection matrix. A positive binding profile is given if a specific binding to the "BCR-of-Interest" is shown. Groups showing such a profile were singulated, and the binding profile of each clone was characterized again on the selection matrix in a second round of selection. Binding of the monoclonal antibodies was verified using a FACS binding assay with a fluorescently labeled anti-mouse IgG antibody. The groups describe: A) no BCR (control); B) a CLL subset2 typical BCR; C) a BCR with arbitrary heavy chain and a CLL subset2 typical light chain; D) a BCR with a CLL subset2 typical heavy chain and an arbitrary light chain; E) a BCR with arbitrary heavy chain and light chain (control; non CLL-Subset2 typical BCR); F) a CLL-Subset2 typical BCR with a mutation in the target motif (R110G) (control). It should be noted that the light chain used in the cases shown in FIGS. 1 B, C and F is the VL3-21 variant.

Based on the finding that the antibody binds only to the cells with the target structures (CLL subset 2 BCR; FIG. 1B), it can be concluded that here is an antibody that binds specifically to cells with autonomously active receptors.

Here, it was shown that the use of cells that are in the pro/pre stage of B-cell development is necessary for the accurate expression of the BCR required for detection. These cells are developmentally genetically set up to display new BCR by exact folding and expression on their surface. Inactivation (knockout) of RAG2 and lambda5 prevents expression of an endogenous BCR and pre-BCR, respectively. Deletion of SLP65 and subsequent reconstruction of an inducible SLP65 allows characterization of the activity level of the "BCR of interest."

To determine the amino acid sequence of monoclonal antibodies selected by selection, mRNA was isolated from each hybridoma clone, cDNA was generated from it and amplified by anchor PCR (Rapid expression cloning of human immunoglobulin Fab fragments for the analysis of antigen specificity of B cell lymphomas and anti-idiotype lymphoma vaccination; Osterroth F, Alkan O, Mackensen A, Lindemann A, Fisch P, Skerra A, Veelken H., J Immunol Methods 1999 Oct. 29; 229 (1-2):141-53).

After identification and sequence determination of the regions important for binding (CDRs), these were transferred to human antibody backbones by PCR. For this purpose, the VH sequence was generated in silico from the human FR regions and the murine CDR regions and subsequently synthesized as DNA fragments. These were then PCR-fused to a human IgG1 and cloned into a vector suitable for expression.

For the generation of the monoclonal antibodies, synthetic peptides representing the regions for the ability of an autonomous signal were used in addition to the complete immunoglobulins.

The specific monoclonal antibody against subset-2 was sequenced and is the subject of separate patent applications.

During sequencing, the following amino acid sequences were determined, where SEQ ID NO. 9 relates to the heavy chain (HC) variable portion, and SEQ ID NO. 10 relates to the light chain (LC) variable portion, and where the highlighted regions denote, in the order indicated, CDR 1, 2, and 3.

```
(AVA-mAb01 HC)
                                      SEQ ID NO. 9
QVQLQQSGPGLVQPSQSLSITCTVSGFSLTSYGIHWVRQSPGKGLEWLGV

IWRGGGTDSNAAFMSRLSITKDNSKSQVFFKMNSLQADDTAIYYCARSRY

DEEESMNYWGQGTSVTVSS
```

-continued (AVA-mAb01 LC)

SEQ ID NO. 10

QIVLTQSPASLSASVGETVTITCRASGNIHSYLAWYQQKQGKSPQLLVYN

AKTLADGVPSRFSGSGSGTQYSLKINSLQPEDFGSYYCQHFWNTPPTFGA

GTKLELK

The partial sequences of the heavy chain corresponding to CDR1, CDR2 and CDR3 according to SEQ ID NO. 9 are indicated in SEQ ID NOS. 11 to 13, while the partial sequences of the light chain corresponding to CDR1, CDR2 and CDR3 according to SEQ ID NO. 10 are shown in SEQ ID NOS. 14 to 16.

```
         SEQ ID NO. 10 (AVA-mAb01 LC)
         (AVA-mAB01 CDR1 HC)
                              SEQ ID NO. 11
         GFSLTSYG (AVA mAB01 CDR2 HC)
                              SEQ ID NO. 12
         IWRGGGT (AVA mAB01 CDR3 HC)
                              SEQ ID NO. 13
         ARSRYDEEESMNY (AVA mAB01 CDR1 LC)
                              SEQ ID NO. 14
         GNIHSY (AVA mAB01 CDR2 LC)
                              SEQ ID NO. 15
         NAKT (AVA mAB01 CDR3 LC)
                              SEQ ID NO. 16
         QHFWNTPPT
```

The procedure described above is exemplary for the generation of antibodies specific to CLL subset 2. The same process was also performed using specific sequences and isotypes for subset 4.

Exemplary CLL subset 4 VH and complete LC DNA segments were synthesized by a contract manufacturer using a standard procedure. These were then fused to a murine IgG1 constant segment by PCR and cloned into a CMV vector. The sequence of the final vector was confirmed by Sanger sequencing.

CLL subset 4 HC (SEQ ID NO. 7):
QVQLQQWGAGLLKPSETLSLTCAVYGGSFSGYYWTWIRQSPGKGLEWIGE

INHSGSTTYNPSLKSRVTISVDTSKNQFSLKLNSVTAADTAVYYCARGYG

DTPTIRRYYYGMDVWGQGTTVTVSSASTKGPSVFPLAPSSKSTSGGTAA

LGCLVKDYFPEPVTVSWNSGALTSGVHTFPACLQSSGLYSLSSVVTVPSS

SLGTQTYICNVNHKPSNTKVDKKC

The areas marked in bold indicate the target sequences (epitopes) of the variable part of the subset 4 BCR heavy chain responsible for its autonomously active state (cf. SEQ ID NOS. 3 and 4).

CLL subset 4 LC (SEQ ID NO. 8):
DIVMTQSPLSLPVTLGQPASISCRSSQSLVHSDGNTYLNWFQQRPGQ

SPRRLIYKVSDRDSGVPDRFSGSGSGTDETLKISRVEAEDVGLYYCM

-continued

QGTHWPPYTFGQGTKVEIKRTVAAPSVFIFPPDEQLKSGTASVVCLL

NNFYPREAKVQWKVDNALQSGNSQESVTEQDSKDSTYSLSSTLTLSK

ADYEKHKVYACEVTHQGLSSPVTKSENRGEC.

Subsequent studies on initially discarded hybridoma cell lines led to the surprising discovery of the present binding molecule according to the invention specific for VL3-21 of the B cell receptor light chain. The respective supernatant of these hybridoma cell lines showed binding to the TKO cell lines as shown in FIG. 1B, 1C, and IF.

The specific monoclonal antibody against B cell receptors with the epitope VL3-21 identified here was sequenced. The following amino acid frequencies were determined, where SEQ ID NO. 25 refers to the variable part of the heavy chain (HC), and SEQ ID NO. 26 refers to the variable part of the light chain (LC), and where the labeled regions denote, in the order indicated, CDR 1, 2, and 3.

```
(AVA-mAb02 HC)
                              SEQ ID NO. 25
QVQLQQPGAELVRPGVSVKISCKGSGYTFTDYAIHWVKQSHAKSLEW

IGVISTYYGDSNYNQKFKGKATMTVNKSSSTAYMELARLTSDDSAIY

YCSRDTSNFDYWGQGTTLTVSS (AVA-mAb02 LC)
                              SEQ ID NO. 26
DIQMTQSPSSMYASLGERVTITCKASQDINSHLTWFQQKPGKSPKTL

IYRANRLVDGVPSRESGSGSGQDYSLTISSLEYEDMGIYYCLQYDEF

PRTFGGGTKLEIK
```

The partial sequences of the heavy chain corresponding to CDR1, CDR2 and CDR3 according to SEQ ID NO. 25 are given in SEQ ID NOS. 19 to 21, while the partial sequences of the light chain corresponding to CDR1, CDR2 and CDR3 according to SEQ ID NO. 26 are shown in SEQ ID NOS. 22 to 24.

```
         (AVA-mAB02 CDR1 HC)
                              SEQ ID NO. 19
         GYTFTDIA (AVA-mAB02 CDR2 HC)
                              SEQ ID NO. 20
         ISTYYGDS (AVA-mAB02 CDR3 HC)
                              SEQ ID NO. 21
         SRDTSNFDY (AVA-mAB02 CDR1 LC)
                              SEQ ID NO. 22
         QDINSH (AVA-mAB02 CDR2 LC
                              SEQ ID NO. 23
         RANR (AVA-m7B02 CDR3 LC)
                              SEQ ID NO. 24
         LQYDEFPRT
```

Example 2

Using the teaching according to the invention, a small amount of peripheral blood was taken from a patient. For analysis, 100 μl of blood was transferred to a reaction vessel and topped with 2 ml of PBS-BSA buffer solution. The sample was then centrifuged in an Eppendorf Centrifuge 5804 at 1500 rpm for a period of five minutes. The supernatant was discarded and the sediment was mixed well. Subsequently, the antibody was added. Staining was performed against the following surface parameters: 1) CD19-FITC, 2) CDS-PE, and 3) the VL3-21 specific antibody (APC) before the mixtures were incubated at room temperature in the dark for 15 minutes. Lysis was then initiated, and the erythrocytes were lysed. As previously described, cells were washed twice with PBS-BSA buffer solution, and cells were picked up and resuspended in 500 µl of 0.1% PBS-BSA buffer solution. Cells were kept in the dark at 2-8° C. until measurement on the flow cytometer.

Analysis on the FACS was performed on a BDCalibur. The setting of the individual laser and detection parameters was performed according to the instructions of the instrument manufacturer and is sufficiently known to the person skilled in the art. The raw data of the analysis were then evaluated using FlowJo analysis software. First, the lymphocyte population was selected and labeled in the FSC/SSC blot. For this selection, we then focused on the CD19-positive B cells and analyzed for binding of the 30 VL3-21 specific antibody. FIG. 2 shows an example of such an analysis using the VL3-21 specific antibody. In a first step, the CD19 positive B cells were selected for further analysis (left panel). These were then analyzed for binding of the specific antibody (right panel).

Example 3

The antibody according to the invention with specificity for a BCR with VL3-21 was used in an apheresis system for the separation of leukemia cells from a blood sample of a patient.

Peripheral blood was collected from one patient (EDTA blood from blood collection tubes). The lymphocyte count was determined using a cell counter and resulted in 80,000 lymphocytes/µl. Immunophenotyping by FACS was performed to determine the "tumor load," i.e. the load of tumor cell material on the sample (using the CLL standard panel WHO tumor load). Secondarily, those cells carrying the CLL epitope were stained with the antibody according to the invention to demonstrate that the cells were positive for this epitope. Then, 500 µl of this blood was mixed with 5×108 MACS MicroBeads (Miltenyi Biotech) conjugated with the specific antibody. The mixture was shaken at room temperature for 5 minutes before the blood was processed over Miltenyi LS columns. Here, the lymphocytes conjugated with the particles (beads) remained on the column, so that blood largely freed from lymphocytes was obtained from the column as a flow-through. After purification twice over the columns (according to the manufacturer's instructions), a lymphocyte count of less than 5000 lymphocytes/µl was detected in a FACS measurement. In a control experiment using blood from a CLL patient without the presence of a BCR with VL3-21 on the leukemia cells, this purification did not result in a significant reduction of B cells in the blood, as expected.

The invention claimed is:

1. A biological binding molecule which selectively binds to B cell receptors, characterized by the presence of a light chain having a sequence according to SEQ ID No. 18, but not to B-cell receptors lacking a light chain according to SEQ ID No. 18, wherein the biological binding molecule is an antibody or a functional fragment thereof having an antigen-binding site, and wherein the biological binding molecule comprises variable parts of a heavy chain corresponding to CDR1, CDR2 and CDR3 given respectively in SEQ ID NO(s). 19, 20 and 21 and variable parts of a light chain corresponding to CDR1, CDR2 and CDR3 given respectively in SEQ ID NO(s). 22, 23 and 24.

2. The biological binding molecule according to claim 1, characterized in that it is in the form of a fusion protein with T-cell specific activation domains.

3. The biological binding molecule according to claim 1, characterized in that it comprises at least one additional region for isolating or killing B-cell neoplasia.

4. A composition of substances comprising a biological binding molecule according to claim 1 for therapeutic purposes.

5. The composition of substances according to claim 4, characterized in that it additionally comprises an antibody or a functional fragment thereof against the light or heavy chain of the B-cell receptor or against the light and heavy chain of the B-cell receptor.

6. The composition of substances according to claim 4, characterized in that the binding molecule is in the form of a fusion protein with T-cell specific activation domains.

7. The composition of substances according to claim 4, characterized in that the binding molecule comprises at least one additional region for isolating or killing B-cell neoplasia.

8. A method of therapy comprising administering to a subject a therapeutically effective quantity of the biological binding molecule according to claim 1.

9. The method of claim 8 for therapy of B-cell malignant neoplasia.

* * * * *

```
                            SEQUENCE LISTING

<160> NUMBER OF SEQ ID NOS: 26

<210> SEQ ID NO 1
<211> LENGTH: 10
<212> TYPE: PRT
<213> ORGANISM: Homo sapiens
<220> FEATURE:
<223> OTHER INFORMATION: Autonom aktiver Bereich Subset 2/1

<400> SEQUENCE: 1

Lys Leu Thr Val Leu Arg Gln Pro Lys Ala
1               5                   10

<210> SEQ ID NO 2
<211> LENGTH: 8
<212> TYPE: PRT
<213> ORGANISM: Homo sapiens
<220> FEATURE:
<223> OTHER INFORMATION: Autonom aktiver Bereich Subset 2/2

<400> SEQUENCE: 2

Val Ala Pro Gly Lys Thr Ala Arg
1               5

<210> SEQ ID NO 3
<211> LENGTH: 10
<212> TYPE: PRT
<213> ORGANISM: Homo sapiens
<220> FEATURE:
<223> OTHER INFORMATION: Autonom aktiver Bereich Subset 4/1

<400> SEQUENCE: 3

Pro Thr Ile Arg Arg Tyr Tyr Tyr Tyr Gly
1               5                   10
```

-continued

<210> SEQ ID NO 4
<211> LENGTH: 9
<212> TYPE: PRT
<213> ORGANISM: Homo sapiens
<220> FEATURE:
<223> OTHER INFORMATION: Autonom aktiver Bereich Subset 4/2

<400> SEQUENCE: 4

Asn His Lys Pro Ser Asn Thr Lys Val
1               5

<210> SEQ ID NO 5
<211> LENGTH: 116
<212> TYPE: PRT
<213> ORGANISM: Homo sapiens
<220> FEATURE:
<223> OTHER INFORMATION: Autonom aktiver Bereich Subset 2 VH

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Ser Ile Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Gln Asn Ala Met Asp Val Trp Gly Gln Gly Thr Thr Val
                100                 105                 110

Thr Val Ser Ser
        115

<210> SEQ ID NO 6
<211> LENGTH: 215
<212> TYPE: PRT
<213> ORGANISM: Homo sapiens
<220> FEATURE:
<223> OTHER INFORMATION: Autonom aktiver Bereich Subset 2 LC

<400> SEQUENCE: 6

Ser Tyr Glu Leu Thr Gln Pro Pro Ser Val Ser Val Ala Pro Gly Lys
1               5                   10                  15

Thr Ala Arg Ile Thr Cys Ala Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Gly Ser Asp His
                85                  90                  95

Pro Trp Val Phe Gly Gly Gly Thr Lys Leu Thr Val Leu Arg Gln Pro
                100                 105                 110

Lys Ala Ala Pro Ser Val Thr Leu Phe Pro Pro Ser Ser Glu Glu Leu

-continued

```
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Cys Ser
    210                 215

<210> SEQ ID NO 7
<211> LENGTH: 224
<212> TYPE: PRT
<213> ORGANISM: Homo sapiens
<220> FEATURE:
<223> OTHER INFORMATION: Autonom aktiver Bereich Subset 4 HC

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Thr Trp Ile Arg Gln Ser Pro Gly Lys Gly Leu Glu Trp Ile
        35                  40                  45

Gly Glu Ile Asn His Ser Gly Ser Thr Thr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gly Tyr Gly Asp Thr Pro Thr Ile Arg Arg Tyr Tyr Tyr Tyr Gly
                100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Cys Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Cys
    210                 215                 220

<210> SEQ ID NO 8
<211> LENGTH: 220
<212> TYPE: PRT
<213> ORGANISM: Homo sapiens
<220> FEATURE:
<223> OTHER INFORMATION: Autonom aktiver Bereich Subset 4 LC
```

-continued

```
<400> SEQUENCE: 8

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asp Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Gly
                85                  90                  95

Thr His Trp Pro Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 9
<211> LENGTH: 119
<212> TYPE: PRT
<213> ORGANISM: Mus musculus
<220> FEATURE:
<223> OTHER INFORMATION: AVA mAb01 HC

<400> SEQUENCE: 9

Gln Val Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Arg Gly Gly Gly Thr Asp Ser Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Ser Arg Tyr Asp Glu Glu Glu Ser Met Asn Tyr Trp Gly Gln Gly
            100                 105                 110

Thr Ser Val Thr Val Ser Ser
            115
```

-continued

```
<210> SEQ ID NO 10
<211> LENGTH: 107
<212> TYPE: PRT
<213> ORGANISM: Mus musculus
<220> FEATURE:
<223> OTHER INFORMATION: AVA mAb01 LC

<400> SEQUENCE: 10

Gln Ile Val Leu Thr Gln Ser Pro Ala Ser Leu Ser Ala Ser Val Gly
1               5                   10                  15

Glu Thr Val Thr Ile Thr Cys Arg Ala Ser Gly Asn Ile His Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Asn Thr Pro Pro
                85                  90                  95

Thr Phe Gly Ala Gly Thr Lys Leu Glu Leu Lys
            100                 105

<210> SEQ ID NO 11
<211> LENGTH: 8
<212> TYPE: PRT
<213> ORGANISM: Mus musculus
<220> FEATURE:
<223> OTHER INFORMATION: AVA mAb01 CDR1 HC

<400> SEQUENCE: 11

Gly Phe Ser Leu Thr Ser Tyr Gly
1               5

<210> SEQ ID NO 12
<211> LENGTH: 7
<212> TYPE: PRT
<213> ORGANISM: Mus musculus
<220> FEATURE:
<223> OTHER INFORMATION: AVA mAb01 CDR2 HC

<400> SEQUENCE: 12

Ile Trp Arg Gly Gly Gly Thr
1               5

<210> SEQ ID NO 13
<211> LENGTH: 13
<212> TYPE: PRT
<213> ORGANISM: Mus musculus
<220> FEATURE:
<223> OTHER INFORMATION: AVA mAb01 CDR3 HC

<400> SEQUENCE: 13

Ala Arg Ser Arg Tyr Asp Glu Glu Glu Ser Met Asn Tyr
1               5                   10

<210> SEQ ID NO 14
<211> LENGTH: 6
<212> TYPE: PRT
<213> ORGANISM: Mus musculus
<220> FEATURE:
<223> OTHER INFORMATION: AVA mAb01 CDR1 LC

<400> SEQUENCE: 14
```

Gly Asn Ile His Ser Tyr
1               5

<210> SEQ ID NO 15
<211> LENGTH: 4
<212> TYPE: PRT
<213> ORGANISM: Mus musculus
<220> FEATURE:
<223> OTHER INFORMATION: AVA mAb01 CDR2 LC

<400> SEQUENCE: 15

Asn Ala Lys Thr
1

<210> SEQ ID NO 16
<211> LENGTH: 9
<212> TYPE: PRT
<213> ORGANISM: Mus musculus
<220> FEATURE:
<223> OTHER INFORMATION: AVA mAb01 CDR3 LC

<400> SEQUENCE: 16

Gln His Phe Trp Asn Thr Pro Pro Thr
1               5

<210> SEQ ID NO 17
<211> LENGTH: 8
<212> TYPE: PRT
<213> ORGANISM: Mus musculus
<220> FEATURE:
<223> OTHER INFORMATION: Autonom aktiver Bereich Subset 4/2

<400> SEQUENCE: 17

Val Ser Ser Ala Ser Thr Lys Gly
1               5

<210> SEQ ID NO 18
<211> LENGTH: 96
<212> TYPE: PRT
<213> ORGANISM: Homo sapiens

<400> SEQUENCE: 18

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

<210> SEQ ID NO 19
<211> LENGTH: 8
<212> TYPE: PRT
<213> ORGANISM: Homo sapiens

<400> SEQUENCE: 19

Gly Tyr Thr Phe Thr Asp Tyr Ala
1               5

-continued

```
<210> SEQ ID NO 20
<211> LENGTH: 8
<212> TYPE: PRT
<213> ORGANISM: Homo sapiens

<400> SEQUENCE: 20

Ile Ser Thr Tyr Tyr Gly Asp Ser
1               5

<210> SEQ ID NO 21
<211> LENGTH: 9
<212> TYPE: PRT
<213> ORGANISM: Homo sapiens

<400> SEQUENCE: 21

Ser Arg Asp Thr Ser Asn Phe Asp Tyr
1               5

<210> SEQ ID NO 22
<211> LENGTH: 6
<212> TYPE: PRT
<213> ORGANISM: Homo sapiens

<400> SEQUENCE: 22

Gln Asp Ile Asn Ser His
1               5

<210> SEQ ID NO 23
<211> LENGTH: 4
<212> TYPE: PRT
<213> ORGANISM: Homo sapiens

<400> SEQUENCE: 23

Arg Ala Asn Arg
1

<210> SEQ ID NO 24
<211> LENGTH: 9
<212> TYPE: PRT
<213> ORGANISM: Homo sapiens

<400> SEQUENCE: 24

Leu Gln Tyr Asp Glu Phe Pro Arg Thr
1               5

<210> SEQ ID NO 25
<211> LENGTH: 116
<212> TYPE: PRT
<213> ORGANISM: Homo sapiens

<400> SEQUENCE: 25

Gln Val Gln Leu Gln Gln Pro Gly Ala Glu Leu Val Arg Pro Gly Val
1               5                   10                  15

Ser Val Lys Ile Ser Cys Lys Gly Ser Gly Tyr Thr Phe Thr Asp Tyr
                20                  25                  30

Ala Ile His Trp Val Lys Gln Ser His Ala Lys Ser Leu Glu Trp Ile
            35                  40                  45

Gly Val Ile Ser Thr Tyr Tyr Gly Asp Ser Asn Tyr Asn Gln Lys Phe
        50                  55                  60

Lys Gly Lys Ala Thr Met Thr Val Asn Lys Ser Ser Ser Thr Ala Tyr
65                  70                  75                  80
```

-continued

```
Met Glu Leu Ala Arg Leu Thr Ser Asp Asp Ser Ala Ile Tyr Tyr Cys
                  85                  90                  95

Ser Arg Asp Thr Ser Asn Phe Asp Tyr Trp Gly Gln Gly Thr Thr Leu
                 100                 105                 110

Thr Val Ser Ser
             115

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Ser Met Tyr Ala Ser Leu Gly
1               5                  10                  15

Glu Arg Val Thr Ile Thr Cys Lys Ala Ser Gln Asp Ile Asn Ser His
                 20                  25                  30

Leu Thr Trp Phe Gln Gln Lys Pro Gly Lys Ser Pro Lys Thr Leu Ile
             35                  40                  45

Tyr Arg Ala Asn Arg Leu Val Asp Gly Val Pro Ser Arg Phe Ser Gly
         50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                 85                  90                  95

Thr Phe Gly Gly Gly Thr Lys Leu Glu Ile Lys
                100                 105
```